United States Patent
Van Waeg et al.

(10) Patent No.: US 9,440,011 B2
(45) Date of Patent: Sep. 13, 2016

(54) HYBRID BLOOD COMPONENT STORAGE BAG AND METHOD OF MAKING SUCH BAG

(71) Applicant: Terumo BCT, Inc., Lakewood, CO (US)

(72) Inventors: Geert Van Waeg, Brussels (BE); Victor D. Dolecek, Englewood, CO (US); Richard Alan Edrich, Denver, CO (US)

(73) Assignee: Terumo BCT, Inc., Lakewood, CO (US)

( * ) Notice: Subject to any disclaimer, the term of this patent is extended or adjusted under 35 U.S.C. 154(b) by 27 days.

(21) Appl. No.: 13/935,843

(22) Filed: Jul. 5, 2013

(65) Prior Publication Data
US 2014/0016883 A1   Jan. 16, 2014

Related U.S. Application Data (60) Provisional application No. 61/670,643, filed on Jul. 12, 2012, provisional application No. 61/670,928, filed on Jul. 12, 2012.

(51) Int. Cl.
*A61J 1/10*    (2006.01)
*A61M 1/02*    (2006.01)

(52) U.S. Cl.
CPC . *A61M 1/02* (2013.01); *A61J 1/10* (2013.01); *A61J 1/1468* (2015.05); *Y10T 156/10* (2015.01)

(58) Field of Classification Search
CPC ................ A61J 1/10; B29K 2027/06; B29K 2015/0038; B29L 2031/7148; A61M 1/0272; A61M 1/0209; A61M 2202/0208; A61M 2202/0225; Y10T 428/1393; Y10T 428/24521
USPC ............. 428/35.7, 68, 98; 383/109; 156/60; 95/46; 260/484.2; 435/307.1
See application file for complete search history.

(56) References Cited

U.S. PATENT DOCUMENTS

| | | |
|---|---|---|
| 4,280,497 A | 7/1981 | Warner et al. |
| 4,455,299 A | 6/1984 | Grode |
| 4,496,361 A | 1/1985 | Kilkson |
| 4,588,401 A | 5/1986 | Kilkson |
| 4,657,542 A | 4/1987 | Ohachi |
| 4,837,047 A | 6/1989 | Sato et al. |
| 5,529,821 A | 6/1996 | Ishikawa et al. |
| 5,639,382 A | 6/1997 | Brown |
| 5,681,273 A | 10/1997 | Brown |
| 5,683,768 A | 11/1997 | Shang et al. |
| 5,772,960 A | 6/1998 | Ito et al. |

(Continued)

FOREIGN PATENT DOCUMENTS

| | | | |
|---|---|---|---|
| EP | 0134896 | * | 5/1984 |
| EP | 0138147 B1 | | 4/1993 |

(Continued)

OTHER PUBLICATIONS

Chong, C. et al., "Simple, rapid methods for measuring the permeability of platelet storage bags to oxygen and carbon dioxide", (Abstract only, unknown publication and date).

(Continued)

*Primary Examiner* — Yan Lan
(74) *Attorney, Agent, or Firm* — René A Pereyra (57) ABSTRACT

A hybrid blood component storage bag having one side of the bag with a greater permeability than another side of the bag and the method of making such bag.

5 Claims, 6 Drawing Sheets

(56) References Cited

U.S. PATENT DOCUMENTS

| | | | |
|---|---|---|---|
| 5,833,866 | A | 11/1998 | Brown |
| 5,958,250 | A | 9/1999 | Brown et al. |
| 6,059,979 | A | 5/2000 | Brown |
| 6,207,063 | B1 | 3/2001 | Brown |
| 6,579,583 | B2 | 6/2003 | Patel |
| 2005/0170019 | A1 | 8/2005 | Roth |
| 2009/0191537 | A1 | 7/2009 | Mayaudon et al. |
| 2011/0097563 | A1 | 4/2011 | Sandford et al. |

FOREIGN PATENT DOCUMENTS

| | | |
|---|---|---|
| EP | 0134896 A2 | 5/1994 |
| EP | 0775010 B1 | 7/2004 |
| EP | 2055767 A1 | 5/2009 |
| GB | 2035093 A | 6/1980 |
| WO | 84/01292 A1 | 4/1984 |
| WO | 2011/004390 A2 | 1/2011 |

OTHER PUBLICATIONS

Heddle, N.M. et al., "In vitro evaluation of prestorage pooled leukoreduced whole blood-derived platelets stored for up to 7 days", Transfusion, Jun. 2005, vol. 45.

Heinz, Robert MT(ASCP)HSBB, "Letter to the Editor: Unacceptable platelet counts and pH in blood bags", Transfusion, 1989, vol. 29, No. 9.

Holme, S.; Heaton, A. and Momada, G., "Evaluation of a new, more oxygen-permeable, polyvinylchloride container", Transfusion, 1989, pp. 159-164, vol. 29, No. 2.

International Search Report and Written Opinion, PCT/US2013/049438, Oct. 21, 2013.

Kakaiya, Ram M. and Katz, Alfred J., "Platelet Preservation in Large Containers", Vox Sang, 1984, pp. 111-118, vol. 46.

Kakaiya, Ram M. M.D., "Correspondence: The Aggregation Defect of Platelets Stored at Room Temperature in New Formulation Plastic Containers", Vox Sang, 1985, pp. 368-369, vol. 49.

Kakaiya, Ram M.; Morse, Edward E. and Panek, Sophia, "Labile Coagulation Factors in Thawed Fresh Frozen Plamsa Prepared by Two Methods", Vox Sang, 1984, pp. 44-46, vol. 46.

Kostelijk, E.H. et al., "Comparison between a new PVC platelet storage container (UPX80) and a polyolefin container", Transfusion Medicine, 2000, pp. 131-139, vol. 10.

Kouketsu, Keiko and Shimizu, Tetsuo, "Storage of Apheresis Platelets in Ethylen-Vinyl Acetate Copolymer Bags: Relationship between the Bag Size and the number of Platelets Maintaining Aerobic Metabolism", Cryobiology, 1988, pp. 440-444, vol. 25.

Moroff, Gary, Friendman, Andrea; and Robkin-Kline, Linda, "Factors Influencing Changes in pH during Storage of Platelet Concentrates at 20-24° C", Vox Sang, 1982, pp. 33-45, vol. 42.

Murphy, S., "Platelet Storage for Transfusion", Thrombozytenlagerung, Beitr. Infusionstherapie Klin. Ernahr., 1986, pp. 93-106, vol. 15, Karger, Basel.

Murphy, Scott and Gardner, Frank, "Platelet Storage at 22° C: Role of Gas Transport Across Plastic Containers in Maintenance of Viability", Blood, Aug. 1975, pp. 209-218, vol. 46, No. 2.

Murphy, Scott, "The Oxidation of Exogenously Added Organic Anions by Platelets Facilitates Maintenance of pH During Their Storage for Transfusion at 22° C", Blood, Apr. 1 1995, pp. 1929-1935, vol. 85, No. 7.

Niu, X.; Whisson, M.E., and Guppy M., "Types and sources of fuels for platelets in a medium containing minimal added fuels and a low carryover plasma", British Journal of Haematology, 1997, pp. 908-916, vol. 97.

Rock, G. et al., "Platelet Storage: An Assessment of the Requirements for Plasma and Oxygen", Transfusion, Mar.-Apr. 1981, pp. 167-177, vol. 21, No. 2.

Rosenstein, Robert Ph.D.; Lawe, John E. M.B., and Gray North, Jane B.S., "pH, P(CO2) and P(O2) in "High-volume" Platelet Concentrates Prepared by Discontinuous-flow Centrifugation and Stored in Polyvinylchloride and Polyethylene Containers", American Society of Clinical Pathologists, Mar. 1980, pp. 397-399.

Shimizu, T. et al., "A Novel Second-Generation Polyolefin Container for Storage of Single-Donor Apheresis Platelets", Vox Sang, 1989, pp. 174-180, vol. 56.

Shimizu, Tetsuo and Kouketsu, Keiko, "Dependence of the number of Platelets Maintaining Aerobic Metabolism on the Size of Storage Containers", Tohoku J. exp. Med., 1988, pp. 91-98, vol. 156.

Wallvik, Jonas and Akerblom, Olof, "Platelet Concentrates Stored at 22° C Need Oxygen: The Significance of Plastics in Platelet Preservation", Vox Sang, 1983, pp. 303-311, vol. 45.

Wallvik, Jonas and Suontaka, Maija, "Limited Metabolic Effect of Mononuclear Cells in Platelet Storage", Thrombosis Research, 1993, pp. 255-264, vol. 70.

Yuasa, Takeshi et al., "Improved extension of platelet storage in a polyolefin container with higher oxygen permeability", British Journal of Haematology, 2004, pp. 153-159, vol. 126.

Zhan, Tong et al., "Influence of Raising Oxygen Content on Function of Platelet Concentrate During Preservation", Journal of Experimental Hematology, 2006, pp. 826-828, vol. 14, No. (4) (English language abstract included).

Zhang, Jerry G. et al., "Buffy-coat platelet variables and metabolism during storage in additive solutions of plasma", Transfusion, May 2008, pp. 847-856, vol. 48.

Office Action, Chinese Patent Application no. 201380036969.8, dated Jul. 15, 2016.

\* cited by examiner

HYBRID BLOOD COMPONENT STORAGE BAG AND METHOD OF MAKING SUCH BAG

CROSS-REFERENCE TO RELATED PATENT APPLICATIONS

This patent application claims priority to U.S. Provisional Patent Application No. 61/670,643 filed on Jul. 12, 2012, entitled HYBRID BLOOD COMPONENT STORAGE BAG AND METHOD OF MAKING SUCH BAG, and U.S. Provisional Patent Application No. 61/670,928 filed on Jul. 12, 2012, entitled HYBRID BLOOD COMPONENT STORAGE BAG AND METHOD OF MAKING SUCH BAG, both provisional applications are hereby incorporated by reference in their entirety as if set forth herein in full.

FIELD

This invention relates to a bag or container for storing blood and blood components for subsequent transfusion to a patient and further relates to the method of making such bag.

BACKGROUND

Blood components, such as platelets, are typically stored for up to five or seven days before subsequent transfusion to a patient. Such platelets for storage are separated from whole blood. Although an apheresis system may be used, platelets may also be separated using a whole blood separator. In this process whole blood is collected from a donor and then subsequently (i.e., eight hours later), the collected whole blood is separated into a platelet product which may be called an interim platelet unit, or IPU. Such platelet product may not be sufficient for a full platelet medical or therapeutic dose. Thus each separated platelet component or IPU will be combined with other platelet products, (which could be from other donors), to form a transfusable dose.

In the past, platelet storage bags or containers for storage of either the IPU or the final platelet product have been made of a single material. Such bags or containers are typically made of polymers such as poly(vinyl chloride), (PVC) or poly-olefins such as SEBS (Styrene-Ethylene-Butylene-Styrene). The polymers are typically compounded with a plasticizer. The polymer material may be heat or high frequency welded together from two plastic sheets of the same material to form the bag. Alternatively, the bag may be blow molded.

Plasticizers compounded with PVC add transparency, flexibility, strength and stability at high and low temperatures to the base PVC polymer. The plasticizers also add permeability to water, oxygen, and carbon dioxide to the base PVC. Although there are a wide range of plasticizers currently available, the choice of plasticizer for blood or blood component contact applications, such as platelet contact applications, are more limited.

The most common plasticizer used for platelet storage containers is di, (2-ethyl hexyl)phthalate (DEHP). Although DEHP adds some permeability to the PVC, the resulting PVC/DEHP material needs to be of a thickness for the necessary carbon dioxide and oxygen permeability.

Another plasticizer suitable for compounding with PVC for blood component contact applications is tri octyl tri mellitate, (TOTM), although such plasticizer is not considered to add as much permeability as DEHP.

Citrate plasticizers have also been used with PVC as a storage bag composition. The use of n-butyrul, tri n-hyxyl citrate (BTHC) plasticizer has been shown to be effective for storing platelets. However, although BTHC plasticizer containers have sufficient oxygen permeability, the carbon dioxide permeability may be such that too much carbon dioxide escapes. Thus the permeability to carbon dioxide may be too great for optimum storage.

Embodiments of the present invention have been made in light of these and other considerations. However, the relatively specific problems discussed above do not limit the applicability of the embodiments of the present invention to solving other problems.

SUMMARY

The summary is provided to introduce aspects of some embodiments of the present invention in a simplified form, and is not intended to identify key or essential elements of the claimed invention, nor is it intended to limit the scope of the claims.

Embodiments relate to a blood component storage bag comprising: a first side consisting of first material formed of a polymer and a first plasticizer wherein the first material has a first permeability; a second side consisting of second material formed of a polymer and a second plasticizer wherein the second material has a second permeability wherein the permeability of one of the first and second sides is greater than the permeability of the other of the first and second sides. It is noted that as used in the present application, the term "blood component" refers to whole blood or a component derived from whole blood, including without limitation, plasma, leukocytes, platelets, red blood cells, and combinations thereof.

Embodiments further relate to a method of manufacturing a blood component storage bag comprising: providing a first sheet of a polymer compounded with a first plasticizer; providing a second sheet of a polymer compounded with a second plasticizer; welding the first sheet to the second sheet to form a bag for blood component storage.

Other embodiments relate to a blood component storage bag comprising: a first sheet of a first polymer; a second sheet of a second polymer; wherein the first sheet has a different permeability to at least one of oxygen or carbon dioxide than the second sheet. In embodiments, the polymer used in the first and second sheet may be the same but each sheet may have a different plasticizer. In other embodiments, the polymers may be different. In yet other embodiments, the polymers may be the same, and have the same plasticizers, but be of different thickness, which results in the different permeabilites.

BRIEF DESCRIPTION OF THE DRAWINGS

Non-limiting and non-exhaustive embodiments are described with reference to the following figures.

DETAILED DESCRIPTION

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Reference will now be made in detail to the embodiments illustrated in the accompanying drawings and described below. Wherever possible, the same reference numbers are used in the drawings and the description to refer to the same or like parts.

Citrate plasticizer as described in the embodiments refers to a citrate ester, such as an alcohol ester of citric acid, which is added to a polymeric material, such as poly(vinyl chloride), to provide desired mechanical, physical, chemical and optical properties, including permeability, flexibility, softness, extensibility, impact resistance or any combination of these. Citrate plasticizers useful in storage bags comprise nontoxic citrate esters. Exemplary citrate plasticizers include n-butyryltri-n-hexyl citrate, triethyl citrate, acetyltriethyl citrate, tri-n-butyl citrate; and acetyltri-n-butyl citrate and combinations thereof.

Polymer as described in the embodiments refers to a molecule comprising a plurality of repeating chemical groups, typically referred to as monomers. Polymers are made more flexible by the addition of plasticizers. Plasticizers also add permeability among other properties to the base polymer. Some non-limiting examples of polymers that may be used in embodiments include poly(vinyl chloride) and poly-olefins such as SEBS (Styrene-Ethylene-Butylene-Styrene).

Di, (2-ethyl hexyl) phthalate, (DEHP), as described in the embodiments is a phthalate that is used as a plasticizer with polymers. It is used to also provide desired properties including permeability, flexibility, softness, extensibility, impact resistance or any combination of these.

Tri octyl tri mellitate, (TOTM), as described in the embodiments is a low volatility plasticizer that is used with polymers as a plasticizer. It also adds the plasticizer characteristics of permeability, flexibility, softness, extensibility, impact resistance or any combination of these.

Figure 1:
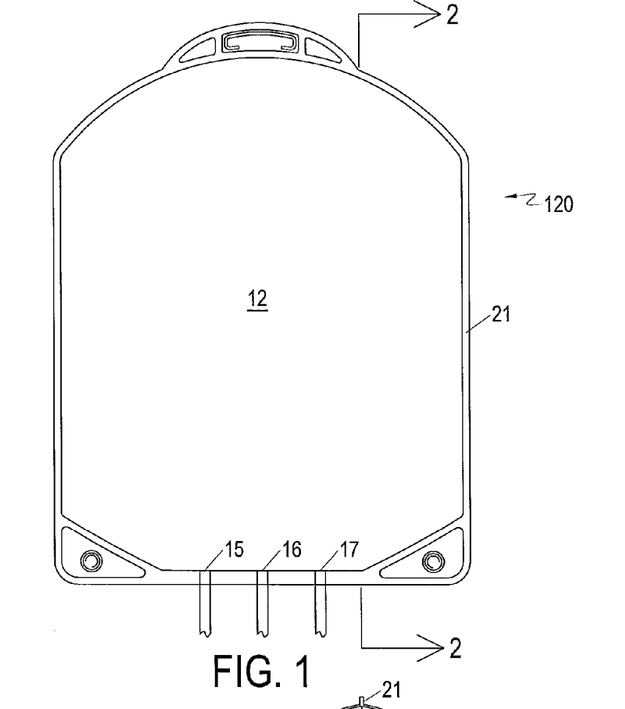
FIG. 1—is a schematic top view of a hybrid platelet storage bag.
Figure 2:
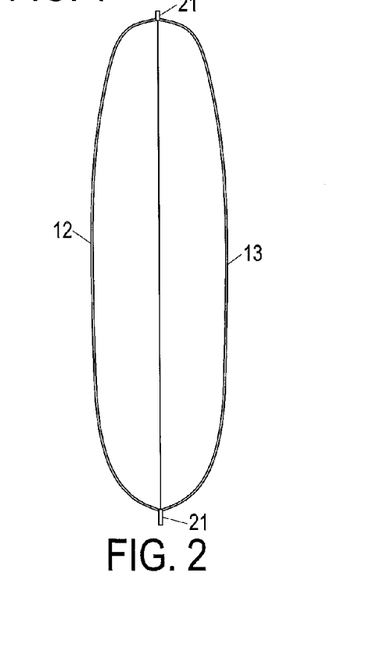
FIG. 2—is a schematic side view of a hybrid platelet storage bag.

FIGS. 1 and 2 provide schematic diagrams of an exemplary container or bag 120 for storing platelets. FIG. 2 is a section taken at line 2-2 of FIG. 1. Such a container includes a first side 12 shown in FIG. 1 formed from citrate plasticized poly(vinyl chloride) sheet material. In one embodiment, the citrate plasticizer may be included in the sheet material in a percentage by weight equal to about thirty eight percent though in other embodiments the amount may vary from about twenty-five percent to about fifty percent by weight.

Several ports, 15, 16, and 17 are shown in the container though it is understood the number and locations of the ports may vary. One port such as 15 may permit fluid such as platelets to enter the container 120. Another port such as 16 may permit fluid such as platelets to exit the container 120. A third port such as 17 may be used for taking a sample of the contents of the container 120. It is understood that the intended use of the ports can also be varied.

The container 120 shown in FIG. 1 has a welded seal 21 around its exterior side 12 as will be more fully described below. In embodiments, the only openings in the welded peripheral seal will be those associated with any ports such as 15, 16, and 17.

FIG. 2 illustrates both sides 12 and 13 in a cross-sectional schematic view of the container 120. The second or other side 13 in the embodiment shown may be formed of TOTM plasticized poly(vinyl chloride) sheet film. The TOTM is also included in the sheet material forming the second side of the container 120. The TOTM may be included in amounts between about 25% and about 50% by weight. In one embodiment, the TOTM comprises about 38% by weight of the sheet material. Also DEHP can be used as the plasticizer in the sheet material of the second side 13. The DEHP may be included in amounts between about 25% and about 50% by weight. In one embodiment, the DEHP comprises about 38% by weight of the sheet material. The cross-sectional view in FIG. 2 shows an embodiment of the peripheral weld 21 connecting the first side 12 to the second side 13.

Figure 3:
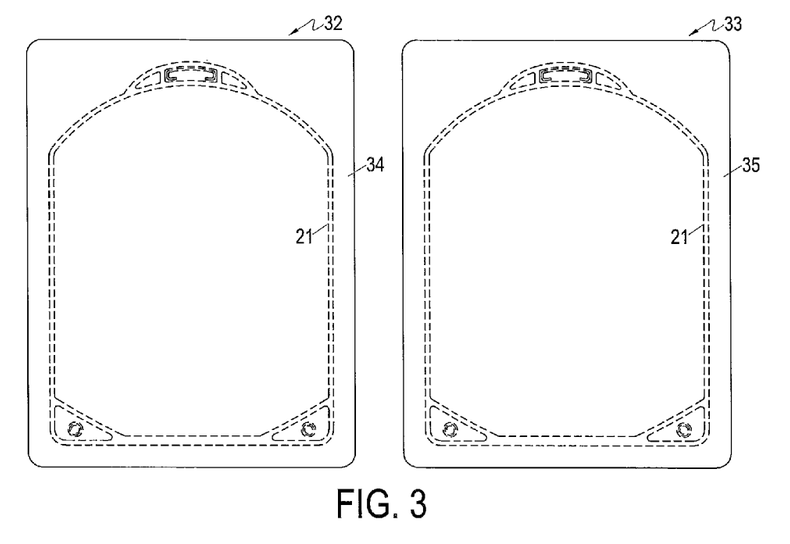
FIG. 3—is a top schematic view of sheet material used to make a hybrid platelet storage bag.
Figure 4:
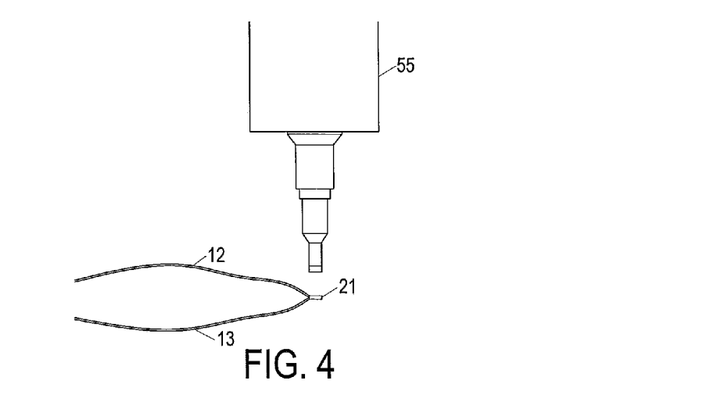
FIG. 4—is a schematic view of a welder welding the sheet material to form a hybrid platelet storage bag.

FIG. 3 illustrates two sheets of polymer material with plasticizer. In embodiments, sheet 32 is formed of PVC with citrate plasticizer. Sheet 33 may be formed of PVC with TOTM plasticizer though DEHP plasticizer could also be used in other embodiments. The proposed weld line 21 is shown in dashed lines on sheets 32 and 33. Such a weld line will seal sheet 32 to 33 to form the container 120. Excess sheet material outside the weld line such as shown at 34 and 35 may be trimmed.

The ports 15, 16, and 17 may be formed of various materials. As one example, the ports may be formed of plasticized PVC so that they may be RF welded to the sheet material. The ports may be inserted between the sheets 32 and 33 where desired such that the weld 21 will seal the sheets around and to the ports. Components made of different polymeric materials may be added to the ports after the ports are welded to the sheet material. For example, frangibles may be created within the ports by inserting polycarbonate components into the ports.

Figure 5:
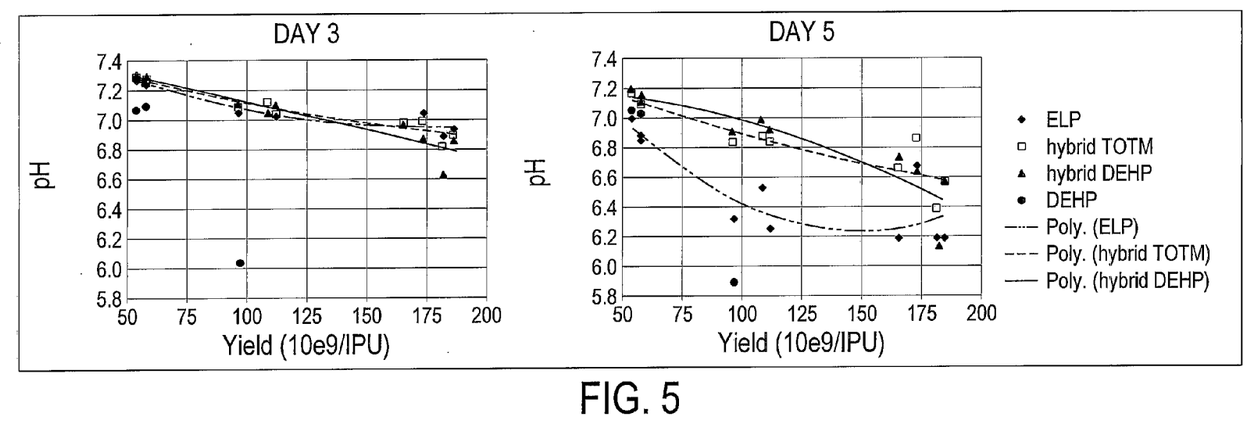
FIG. 5—is graph indicating the pH level of an IPU storage bag at both Day 3 and Day 5 of storage.

The weld 21 may be formed by high frequency or other known welding methods. FIG. 5 schematically illustrates an embodiment of a welder 55 welding the sheet 32 to the sheet 33 around its peripheral edge.

In embodiments, the citrate plasticizer for the PVC material of sheet 32 to form one side 12 may be selected from a group of citrate plasticizers, including n-butyryltri-n-hexyl citrate, triethyl citrate, acetyltriethyl citrate; and acetyltri-n-butyl citrate or combinations of such citrates.

The permeability of the materials that may be used to form embodiments of a hybrid bag is listed in the table below.

TABLE 1

| Material | Permeability ml/m2/day | | |
|---|---|---|---|
| | 02 | CO2 | CO2/02 |
| PVC/DEHP | 450 | 3500 | 7.8 |
| PVC/TOTM | 750 | 5100 | 6.8 |
| PVC/Citrate | 2260 | 20181 | 8.9 |

Hybrid bags formed with one side of PVC/DEHP or PVC/TOTM and the other side of PVC/citrate would provide a bag wherein one side, (the PVC/citrate side), had a permeability greater than the other side, (the PVC/DEHP or PVC/TOTM side). This embodiment would conserve CO2 through the one side with the lower permeability, (the PVC/DEHP or PVC/TOTM side), while permitting O2 introduction and supply through the side having the higher permeability, (the PVC/citrate side).

Embodiments may be formed of sheet material having different permeabilities as described above. In one embodiment, the difference in permeabilities may be based, at least in part, on different thicknesses. For example, in one embodiment, a bag may be made of the same polymer/plasticizer but be formed with one side of a first thickness and a second side of a second thickness. In other embodiments, the difference in permeabilities may be based on a combination of different polymers/plasticizers and also different thicknesses for each side of the bag.

Example 1

In the examples below, the properties of embodiments of a hybrid bag 120 will be described in greater detail as compared to bags formed of PVC with the same plasticizer for the entire bag.

The following example illustrates five-day storage of platelets forming an interim platelet unit, (IPU) separated from whole blood. The IPUs are stored for 5 days at between about 20° C. and about 24° C. under standard blood bank conditions.

In the example, IPUs are pooled (3 to 10 IPUs per pool) and split into 4 different types of test bags as described below. Target plasma content per IPU is 45-55 ml. In case the pool volume is too small to end up with the target plasma content, blood type matched or ABO-matched plasma is added to bring the volume into the target range. When splitting the pooled platelets into the bags, all the available air is removed so that no air is present in any of the test bags. This provides a condition in the bags that is slightly different than a normal platelet product for storage in that less air is available. The presence of the air, normally present in a storage bag or container, may typically have some positive effect on storage due to the oxygen provided.

Ten pools are made on day 1 after overnight whole blood processing on the Atreus Whole Blood Separation System manufactured by Terumo BCT, Inc., Lakewood, Colo. USA. The IPUs are approximately six (6) hours old by the time they are pooled. The pools are sampled on day 3 and 5 (in the morning). Glucose is measured using a small FreeStyle Lite® glucose meter, available from Abbott Laboratories, of Abbott Park, Ill. USA. Blood gases and pH are measured at 37° C. with the Siemens RapidLab® 348 blood gas analyzer, available from Siemens Healthcare of Tarrytown, N.Y., USA. Platelet and WBC counts and mean platelet volume, (MPV), is measured by a Coulter LG available from Beckman Coulter, Inc. of Brea, Calif., USA. The platelet yields present in the tested bags are spread between 50 and 185×10e9/IPU.

The lines on the graphs of FIGS. 5 through 12 are second order polynomial regression lines.

For this example, four different types of bags are used. Each of the four bags is of the same shape and size. Each of the bags is sterilized using an autoclave or steam sterilization process. All of the bags have the same label.

1. Bag 1 is made of a single material which is PVC compounded with citrate plasticizer. In FIGS. 5 to 12, Bag 1 is designated as the "ELP" bag.

2. Bag 2 is a hybrid citrate/DEHP bag with one side formed of PVC material with DEHP plasticizer and the second side formed of PVC with citrate plasticizer (label on the DEHP side). In FIGS. 5 to 12 this is designated as the "hybrid DEHP" bag.

3. Bag 3 is a hybrid citrate/TOTM bag with one side formed of PVC material with TOTM plasticizer and the second side formed of PVC material with citrate plasticizer, (label on the TOTM side). In FIGS. 5-12 this is designated as the "hybrid TOTM" bag.

4. Bag 4 is made of a single material which is PVC compounded with DEHP plasticizer. In FIGS. 5-12 this bag is designated as the DEHP bag.

FIG. 5 indicates the pH level at both Day 3 and Day 5 of storage for the different IPU units containing different yields of platelets. An acceptable pH for platelet storage is considered to be within the range 6.2 to 7.6 pH. There was little variation between the hybrid TOTM and hybrid DEHP bags and the ELP bag at day 3. At day 5, pH is acceptable for all units in both the hybrid TOTM and hybrid DEHP bags except the unit at 181×10e9 platelets (but acceptable at 165, 173 and 184×10e9 platelets). The ELP bag performs much weaker starting from a yield around 95×10e9 plt/IPU and upwards in yield. Overall, no difference is seen between the hybrid TOTM and hybrid DEHP bags.

Figure 6:
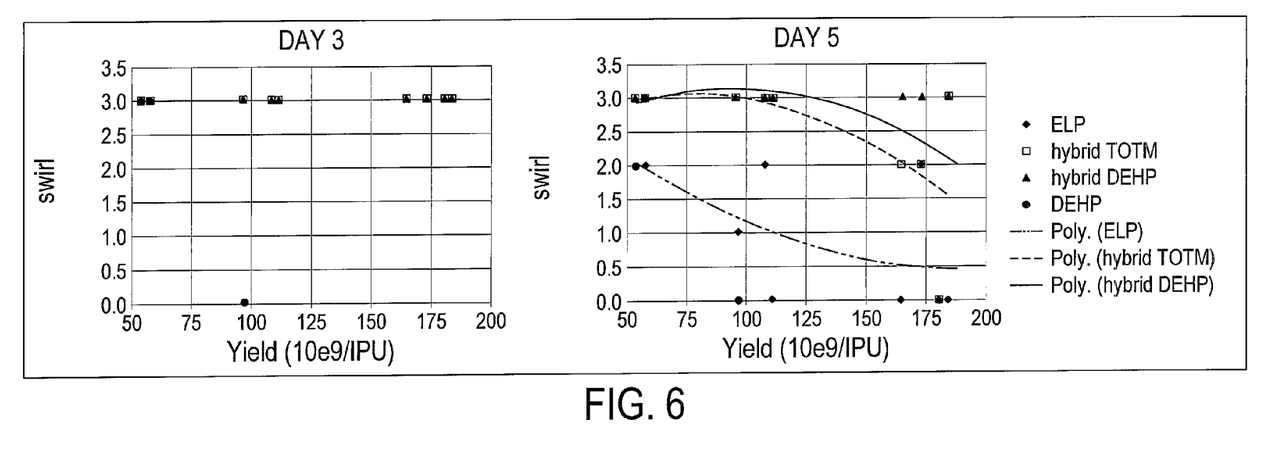
FIG. 6—is a graph indicating the swirl of stored IPUs at both Day 3 and Day 5 of storage.

FIG. 6 indicates the swirl of the platelets at Day 3 and Day 5 of storage. As is understood by those of skill in the art, swirl is a qualitative test done to assess platelet quality. It is a visual test based on the phenomena that suspended platelets tend to "swirl" due to their discoid shape. Scores are assigned from worst to best. Examples of scoring scales include 0-3 (with higher numbers indicating higher swirl) and 1-3 (with higher numbers indicating higher swirl). Healthy platelets have a discoid shape and readily swirl, which result in a score of 3. Unhealthy or stressed platelets lose their discoid shape, do not swirl, and would result in scores less than 3. Lack of platelet swirl indicates decreased platelet viability. The swirl is acceptable for all tested bags at day 3 except for the DEHP bag. At day 5, both the hybrid TOTM and hybrid DEHP bags indicate more platelet swirl than the other bags. No significant difference in swirl is detected between hybrid TOTM and hybrid DEHP bags.

Figure 7:
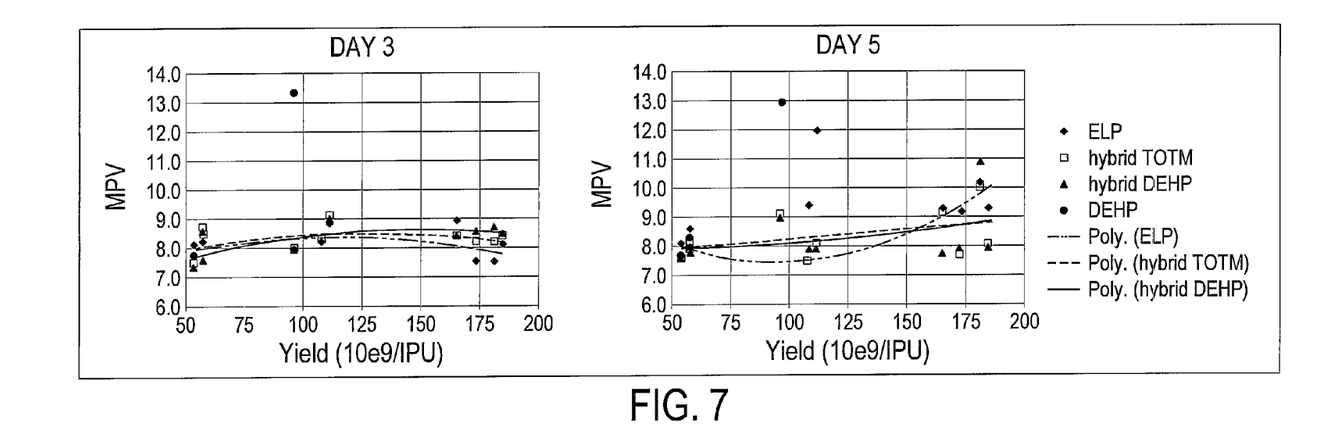
FIG. 7—is a graph indicating the mean platelet volume of stored IPUs at both Day 3 and Day 5 of storage.

FIG. 7 indicates the mean platelet volume or MPV at Day 3 and Day 5. All MPVs remain at an acceptable range of 7-10 fl (femto liters) for the hybrid DEHP and hybrid TOTM bags up to day 5. The ELP bag shows inferior performances from 95×10e9 plt/IPU upwards. No difference is seen between the hybrid TOTM and hybrid DEHP bags.

Figure 8:
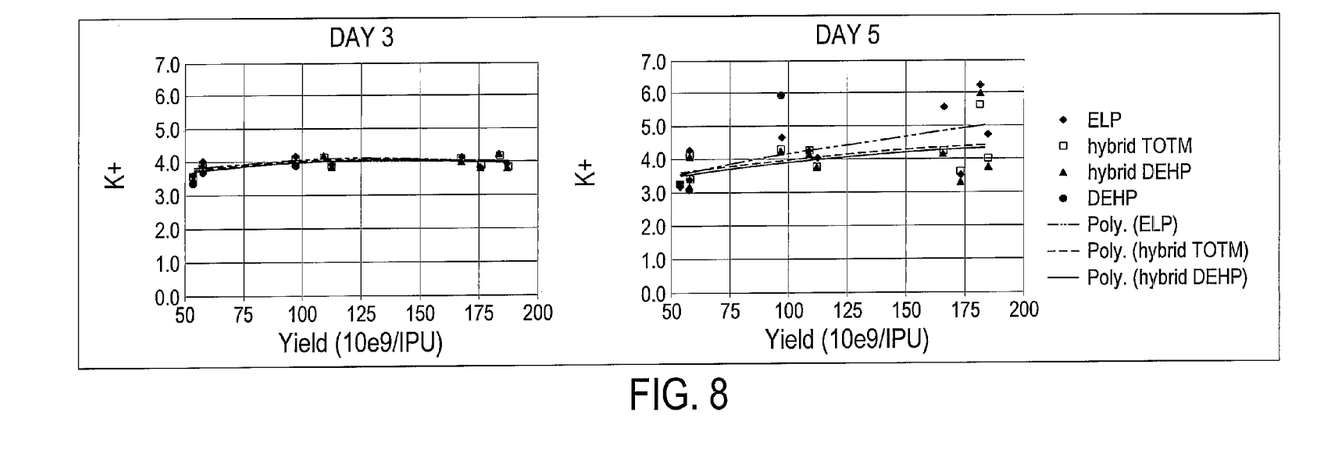
FIG. 8—is a graph indicating the potassium levels in IPU storage bags at both Day 3 and Day 5 of storage.

FIG. 8 indicates the potassium, (K+), levels for the platelets in the four bags at Day 3 and Day 5. Maintenance of potassium indicates good platelet viability. Release of potassium by the platelets, indicated by an overall increase of potassium in the bag, may indicate platelet damage or rupture. The hybrid DEHP and the hybrid TOTM bags maintain their potassium levels with only a slight increase at up to five days for high yields. The ELP bag shows slight increase in potassium.

Figure 9:
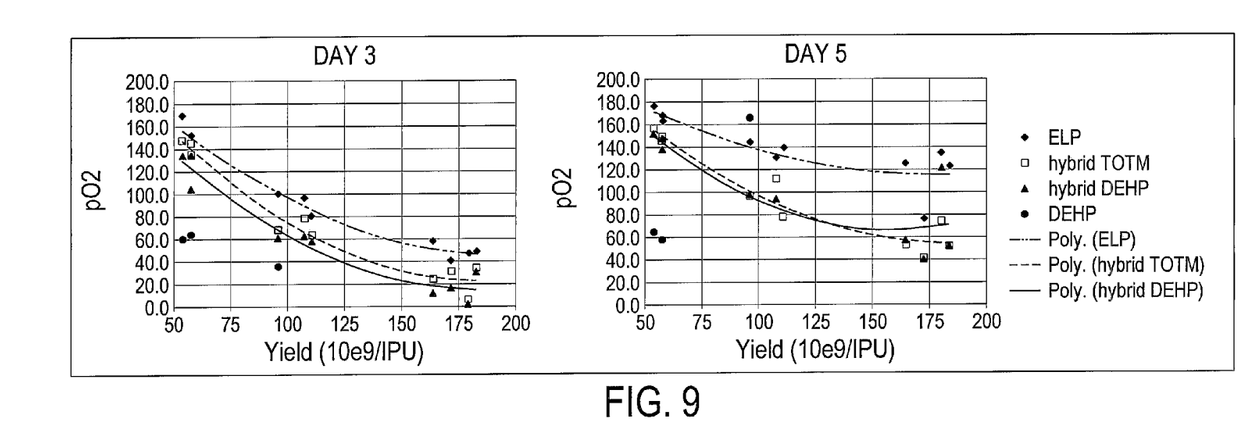
FIG. 9—is a graph indicating the oxygen amount available in IPU storage bags for stored IPUs at both Day 3 and Day 5 of storage.
Figure 10:
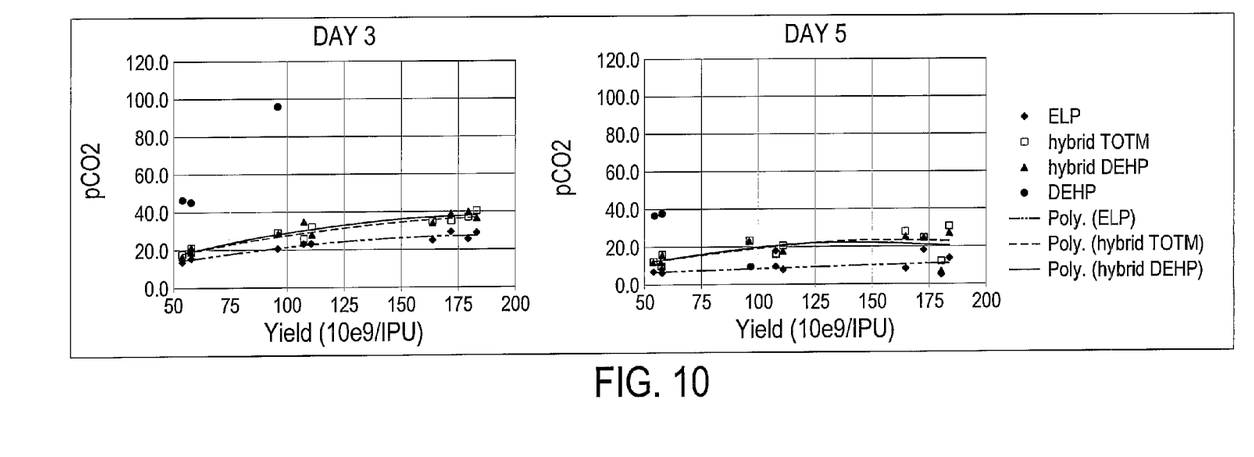
FIG. 10—is a graph indicating the carbon dioxide amount available in IPU storage bags for stored IPUs at both Day 3 and Day 5 of storage.

FIGS. 9 and 10 indicate the oxygen and carbon dioxide levels in the bags at Day 3 and Day 5. Although permeability is necessary for good platelet storage, oxygen, (pO2) can add to platelet life while loss of too much carbon dioxide, (CO2 or pCO2), can be an indication of decreased platelet viability. At day 3, the oxygen levels, (pO2) are higher and the CO2 levels lower in the ELP bag than in the hybrid TOTM and hybrid DEHP bags. The DEHP-only bag shows even lower pO2 and higher pCO2 levels.

The pO2 and pCO2 profiles at day 5 suggest that there is aerobic metabolism in most of the bags over the full range, with the exception of the ELP bag. The pCO2 levels in the hybrid TOTM and hybrid DEHP bags are approximately twice those in the ELP bag. Both hybrid bags show a very similar profile with respect to pCO2, while there is some indication that the pO2 levels in the hybrid TOTM bag is slightly higher than that in the hybrid DEHP bag.

Figure 11:
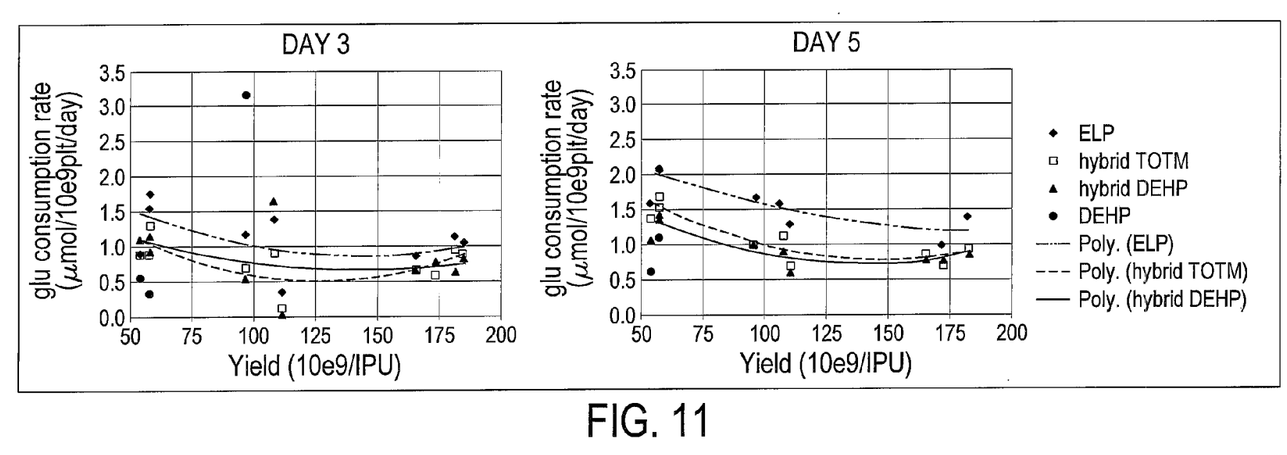
FIG. 11—is a graph indicating the glucose consumption rate of stored IPUs at both Day 3 and Day 5 of storage.
Figure 12:
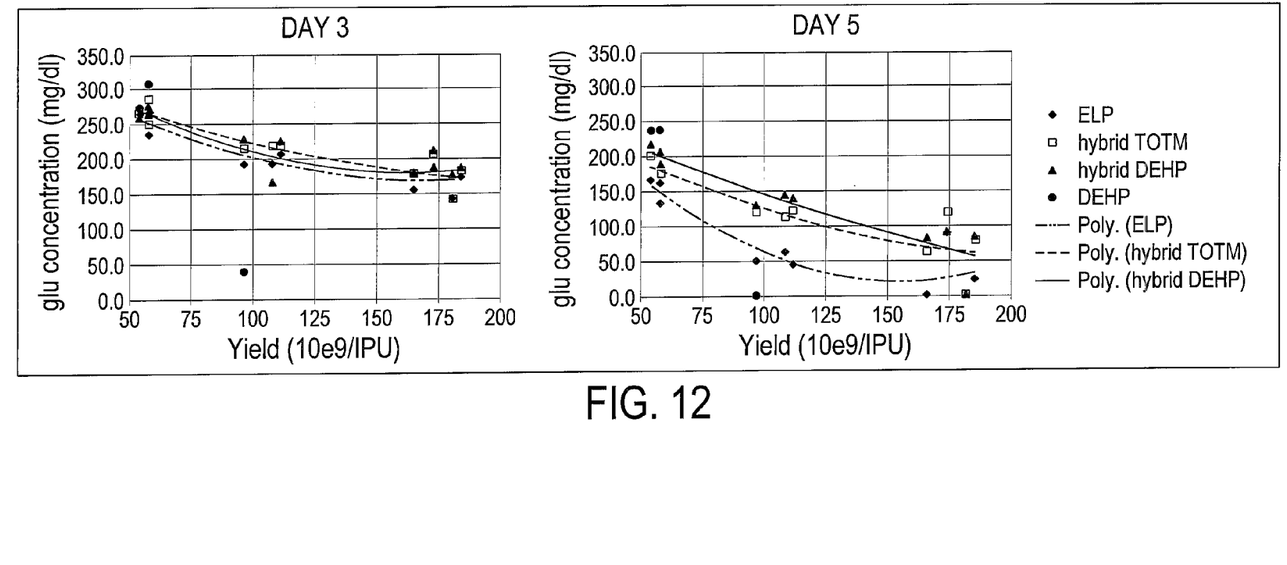
FIG. 12—is a graph indicating the glucose concentration available in IPU storage bags for stored IPUs at both Day 3 and Day 5 of storage.

FIGS. 11 and 12 indicate the glucose consumption rate, (FIG. 11) and the glucose concentration rate (FIG. 12) for 3 day and 5 day storage. As shown in FIG. 11 the glucose consumption rate is in the range 0.5-1.5 µmol/10e9 plt/day in both the hybrid TOTM and the hybrid DEHP bags, with the typical higher consumption levels at lower IPU yields. The ELP bag shows a higher glucose consumption rate, in the order of 50% higher. Similarly at Day 5 the glucose consumption rate for the ELP bag is higher with corresponding low glucose concentration.

The above described figures and data indicate the performance of the hybrid TOTM and hybrid DEHP bags for 5 day IPU storage. The data also confirms that the hybrid TOTM bag performs similar to the hybrid DEHP bags such that the hybrid TOTM bag could be substituted for the hybrid DEHP bag with comparable platelet survival. The data further suggests that the CO2 preservation in the bag and thus the pCO2 levels might be an important influence of anaerobic metabolism (glycolysis). These studies further indicate the importance of having enough oxygen supply while not losing too much CO2.

Example 2

A hybrid bag is tested by storing platelets for five (5) days. The hybrid bag is made from PVC using two different plasticizers. One side of the bag is made from PVC with a citrate plasticizer. The other side of the bag is also made from PVC but instead uses TOTM as a plasticizer.

The study includes three Arms each of which tested a different volume. The table below summarizes the conditions and the results for the three Arms of the study.

TABLE 2

|  | Arm 1 Target 50 ml | | Arm 2 Target 30 ml | | Arm 3 Target 20 ml | |
| --- | --- | --- | --- | --- | --- | --- |
|  | Fresh | Overnight | Fresh | Overnight | Fresh | Overnight |
| Average of Product Volume (ml) Day 5 before sampling | 49.7 | 48.7 | 35.1 | 33.3 | 23.2 | 26.6 |
| Min of Product Volume (ml) Day 5 before sampling | 43.4 | 44.1 | 30.6 | 31.7 | 20.1 | 25.0 |
| Max of Product Volume (ml) Day 5 before sampling | 53.3 | 53.8 | 39.7 | 38.1 | 26.2 | 28.7 |
| Average of Platelet Concentration in IPU (E3/µl) Day 5 | 1271 | 1796 | 1730 | 2625 | 2793 | 3723 |
| Min of Platelet Concentration in IPU (E3/µl) Day 5 | 685 | 1279 | 334 | 1824 | 1566 | 1583 |
| Max of Platelet Concentration in IPU (E3/µl) Day 5 | 1671 | 2321 | 4795 | 4638 | 4010 | 6421 |
| Average of Total PLT in Post Product (E9) Day 5 | 63.1 | 87.3 | 61.4 | 87.1 | 65.5 | 97.5 |
| Max of Total PLT in Post Product (E9) Day 5 | 80.6 | 115.5 | 164.7 | 147.3 | 86.5 | 162.3 |
| Min of Total PLT in Post Product (E9) Day 5 | 34.1 | 64.5 | 10.3 | 61.0 | 31.4 | 42.4 |

Below is a table summarizing the number of IPU's for each Arm of the study.

TABLE 3

Number of IPU's Stored in the Categories of Targets

|  | Fresh | Overnight | Target |
| --- | --- | --- | --- |
| Day 5 Low IPU volume x < 30.0 | 7 | 7 | 6 per each condition |
| Day 5 IPU volume range 31-40 | 17 | 14 | 10 per each condition |
| Day 5 IPU volume range 41-higher | 11 | 11 | 10 per each condition |

The results of the above study indicate that a wide range of platelet volume/concentration combinations store well in the citrate/TOTM bag for up to five (5) days.

It will be apparent to those skilled in the art that various modifications and variations can be made to the methods and structure of the present invention without departing from its scope. Thus it should be understood that the present invention is not limited to the specific examples given. Rather, the invention is intended to cover modifications and variations within the scope of the following claims and their equivalents. Various modifications, changes, and variations apparent to those skilled in the art may be made in the arrangement, operation, and details of the methods and systems of the present invention disclosed herein without departing from the scope of the claimed invention.

What is claimed is:

1. A blood component storage bag for storing platelets, the bag comprising:
   a first sheet of a first polymer, wherein the first sheet comprises a citrate plasticizer;

a second sheet of a second polymer, wherein the second sheet comprises tri octyl tri mellitate (TOTM) plasticizer;

wherein the second sheet has a lower permeability to carbon dioxide than the first sheet to conserve carbon dioxide in the blood component storage bag.

2. The blood component storage bag of claim 1 wherein the first polymer is the same as the second polymer.

3. The blood component storage bag of claim 1 wherein the first sheet is thicker than the second sheet.

4. The blood component storage bag of claim 1 wherein the first polymer comprises poly (vinyl chloride).

5. The blood component storage bag of claim 1 wherein the citrate plasticizer comprises a plasticizer selected from the group consisting of:

n-butyryltri-n-hexyl citrate, triethyl citrate, acetyltriethyl citrate; and acetyltri-n-butyl citrate or combinations of such citrates.

\* \* \* \* \*